United States Patent
Flemming et al.

(10) Patent No.: US 6,916,934 B2
(45) Date of Patent: Jul. 12, 2005

(54) PROCESS FOR PREPARING PYRIDINE-SUBSTITUTED AMINO KETAL DERIVATIVES

(75) Inventors: Hans-Wolfram Flemming, Usingen (DE); Gerhard Korb, Hainburg (DE); Juergen Mueller-Lehar, Weinolsheim (DE); Walter Weber, Hofheim (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 26 days.

(21) Appl. No.: 10/764,810

(22) Filed: Jan. 26, 2004

(65) Prior Publication Data

US 2004/0158073 A1 Aug. 12, 2004

Related U.S. Application Data

(60) Provisional application No. 60/482,295, filed on Jun. 25, 2003.

(30) Foreign Application Priority Data

Feb. 11, 2003 (DE) .......................................... 103 05 391

(51) Int. Cl.⁷ ...................... C07D 213/38; C07D 213/53
(52) U.S. Cl. ....................................... 546/334; 546/338
(58) Field of Search .................................. 546/334, 338

(56) References Cited

U.S. PATENT DOCUMENTS

| | | | |
|---|---|---|---|
| 4,746,669 A | 5/1988 | Caldwell et al. |
| 5,635,485 A | 6/1997 | Agouridas et al. |
| 5,792,871 A | 8/1998 | Chartrain et al. |

FOREIGN PATENT DOCUMENTS

| EP | 0291673 | 11/1988 |
|---|---|---|

OTHER PUBLICATIONS

Shargi et al, Synlett, vol. 2001, issue 1, p. 99–101 (2001).*
Sharma et al, J. of Organometallic Chem. vol. 664, p. 66–69 (2002).*

George Roger Clemo et al., The Synthesis of Phenyl– and Pyridyl–glyoxalines, Journal Am. Soc. (1938, pp. 753–755, vol. 53).

John Y.L. Chung et al., Practical Chemoenzymatic Synthesis of a 3–Pyridylethanolamino Beta3 Adrenergic Receptor Agonist, Tetrahedron Letters (1999, pp. 6739–6743, vol. 40).

Houben–Weyl 11/1: Stickstoffverbindungen II, (1957, S. pp. 903–905).

\* cited by examiner

Primary Examiner—Bernard Dentz
(74) Attorney, Agent, or Firm—Joseph Strupczewski

(57) ABSTRACT

The present invention relates to an efficient process for preparing derivatives of 1-(pyridinyl)-1,1-dialkoxy-2-aminoethane of the formula (I), with which compounds of the formula (I) can be prepared in high purity and yield and in the form of the free base without isolating the acetylpyridine oxime of the formula (XI) which is a critical product from a safety point of view as a solid.

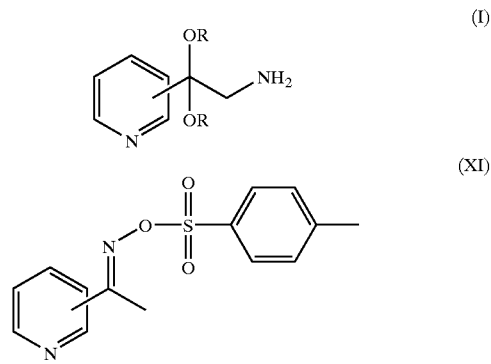

18 Claims, No Drawings

PROCESS FOR PREPARING PYRIDINE-SUBSTITUTED AMINO KETAL DERIVATIVES

This application claims the benefit of priority of German Patent Application No. 10305391.3, filed Feb. 11, 2003 and the benefit of U.S. Provisional Application No. 60/482,295 filed Jun. 25, 2003.

The present invention provides a process for preparing pyridinyl-substituted dialkoxyaminoethane derivatives of the formula (I) and intermediates in the process according to the invention.

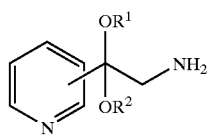
(I)

The compounds of the formula (I) are intermediates in the preparation of active pharmaceutical ingredients. For example, U.S. Pat. No. 5,792,871 describes the synthesis of derivatives of a compound of the formula (I) in which the pyridine radical is substituted in the 3-position and R' is $(C_1-C_3)$-alkyl. Starting from these derivatives, according to U.S. Pat. No. 5,792,871, compounds of the formula (II) are obtainable.

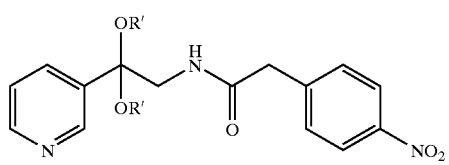
(II)

In addition, compounds of the formula (I) are used as a building block for preparing pyridinoimidazole derivatives of the formula (III) (J. Am. Soc., 1938, 753–755)

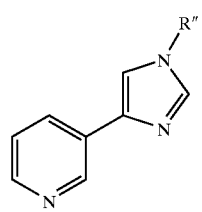
(III)

where R" is H, SH.

Derivatives of the pyridinoimidazole of the formula (III) were used in turn for preparing novel macrolide antibiotics, for example telithromycin (U.S. Pat. No. 5,635,485).

Known processes for preparing compounds of the formula (I) are based on the action of alkali metal alkoxides on p-toluenesulfonic esters of ketoximes in alcoholic solution, for example amino ketal derivatives of the formula (I) occur as an intermediate in the preparation of cyclic amino ketones (F. Möller: Amine durch Umlagerungsreaktionen (Neber-Umlagerung) [Amines by rearrangement reactions (Neber rearrangement)], Houben-Weyl 11/1: Stickstoffverbindungen II [Nitrogen compounds II] (1957), p. 903–905).

The preparation of 1-(pyridinyl)-1,1-dialkoxy-2-aminoethane derivatives of the formula (I) is described in the U.S. Pat. No. 5,792,871 using the example of the 1-(3-pyridinyl)-1,1-diethoxy-2-aminoethane dihydrochloride of the formula (IV) by the following three-stage process:

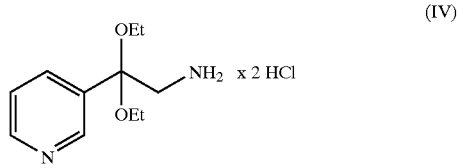
(IV)

In this method, 3-acetylpyridine of the formula (V) is initially oximated with hydroxylammonium chloride in methanol. The resulting 3-acetylpyridine oxime of the formula (VI) is converted to pyridine by a solvent change and is dried by a plurality of distillation procedures and also by addition of fresh pyridine (water content <5 mol %).

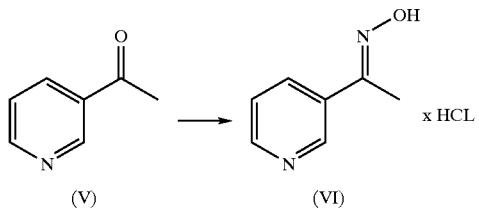
(V)        (VI)

Alternatively, the oximation is carried out directly in pyridine and drying is effected in the same manner. The resulting mixture of the hydrochloride of 3-acetylpyridine oxime of the formula (VI) and pyridine is subsequently reacted with tosyl chloride of the formula (VII) to give 3-acetylpyridine tosyl oxime of the formula (VIII), precipitated from the mixture with water and isolated.

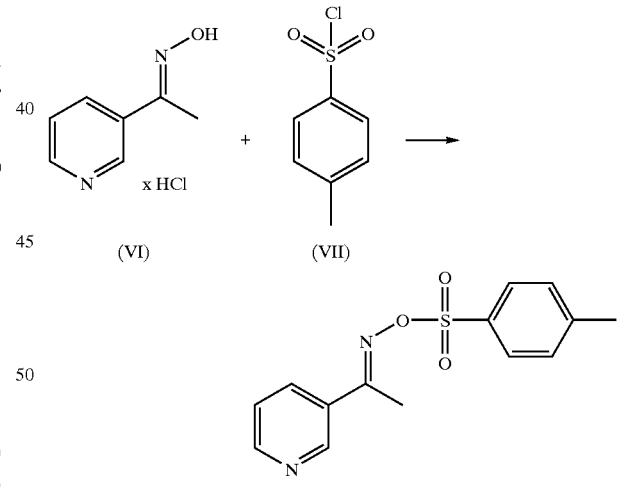
(VIII)

The resulting tosyl oxime of the formula (VIII) is subsequently reacted with potassium ethoxide in ethanol in a Neber rearrangement to give the amino ketal. The resulting p-toluenesulfonic acid potassium salt is filtered after dilution with methyl tert-butyl ether and the filtered solution is admixed with hydrogen chloride dissolved in ether. This precipitates the 1-(3-pyridinyl)-1,1-diethoxy-2-aminoethane dihydrochloride of the formula (IV) as an orange-colored solid.

According to U.S. Pat. No. 5,792,871, the purity of the isolated product could only be estimated with the aid of $^1$H and $^{13}C$ NMR data to >95% as a consequence of unknown impurities. For the further reaction, the amino ketal dihydrochloride (IV) is suspended in water and admixed with sodium hydroxide solution, in order to prepare the amino ketal as the free base which is required for the further coupling reaction.

The above-described process has some disadvantages for the scale-up to the industrial scale: first, the intermediates obtained each have to be dried by distillation procedures. Second, the 3-acetylpyridine tosyl oxime intermediate of the formula (VIII) decomposes very easily in the event of prolonged storage above room temperature to release large amounts of energy (decomposition energy for 3-acetylpyridine tosyl oxime approx. 1000 J/g, see also warning with regard to the storage of a toluenesulfonic ketoxime ester in F. Möller: Amine durch Umlagerungsreaktionen (Neber-Umlagerung), Houben-Weyl 11/1: Stickstoffverbindungen II (1957), p. 903–905). Third, the 1-(3-pyridinyl)-1,1-diethoxy-2-aminoethane dihydrochloride (IV) prepared in this way is contaminated by by-products, which is confirmed by the strong coloration. Fourth, in order to obtain the free 1-(3-pyridinyl)-1,1-diethoxy-2-aminoethane, the isolated salt (IV) has to be released with an auxiliary base in an additional step. Fifth, there are frequent solvent changes during the process. The solvent mixtures then have to be worked up again very expensively, which leads to environmental pollution.

It is an object of the present invention to find a more efficient and safe process for synthesizing the compounds of the formula (I).

The present invention therefore provides a process for preparing 1-pyridinyl-1,1-dialkoxy-2-aminoethane derivatives of the formula (I) where $R^1$ and $R^2$ are each independently $(C_1-C_6)$-alkyl, where the alkyl group may be straight-chain or branched, or where $R^1$ and $R^2$ together with the oxygen atoms form a cyclic ketal in which $R^1$ and $R^2$ together are a $(C_2-C_4)$-alkylidene group, and where the pyridine radical is substituted in the 2-, 3- or 4-position, preferably in the 3-position, which comprises, in process step (a), converting acetylpyridine of the formula (V) using an aqueous solution of a hydroxylammonium compound, for example hydroxylammonium chloride or hydroxylammonium sulfate, or an aqueous solution of hydroxylamine, with the simultaneous or later addition of an inorganic base comprising $M^{n+}$, to the acetylpyridine oxime metal salt of the formula (IX) where n is 1 or 2 and $M^{n+}$ is an alkali metal metal ion where n=1 or alkaline earth metal ion where n=2, preferably $Li^+$, $Na^+$, $K^+$ or $Ca^{2+}$.

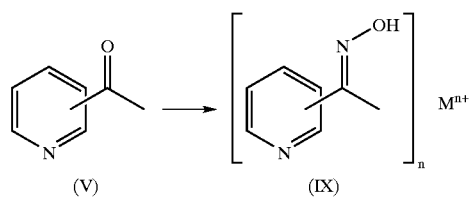

(V)      (IX)

$R^1$ and $R^2$ are preferably each a $(C_1-C_6)$-alkyl radical. Particular preference is given to $R^1$ and $R^2$ being the same and each being a $(C_1-C_6)$-alkyl radical. $(C_1-C_6)$-Alkyl is, for example, methyl, ethyl, n-propyl, isopropyl, n-butyl, isobutyl or n-hexyl.

The cyclic ketal containing a $(C_2-C_4)$-alkylidene group is, for example, a [1,3]dioxolane or a [1,3]dioxane radical.

The preparation can be effected batchwise or continuously by single- or multicomponent metering. The compound of the formula (IX) can be isolated or further processed as a solution or suspension.

$M^{n+}$ is, for example, $Li^+$, $Na^+$, $K^+$ or $Ca^{2+}$. Inorganic bases comprising $M^{n+}$ are, for example, alkali metal or alkaline earth metal hydroxides, alkali metal or alkaline earth metal carbonates or alkali metal or alkaline earth metal hydrogencarbonates or mixtures thereof, preferably lithium hydroxide, sodium hydroxide, potassium hydroxide, calcium hydroxide, sodium carbonate, sodium hydrogencarbonate or potassium carbonate.

For 100 mol of acetylpyridine, preference is given to using 98–120 mol of hydroxylamine or hydroxylammonium compound, more preferably 99–101 mol; and also 200–300 mol of an inorganic base comprising $M^+$, more preferably 200–220 mol, or 100–150 mol of an inorganic base comprising $M^{2+}$, more preferably 100–110 mol.

In process step (b), the aqueous solution, the aqueous suspension or the isolated solid of acetylpyridine metal salt of the formula (IX) is reacted with a solution of a p-toluenesulfonic acid derivative (X) containing a leaving group Y

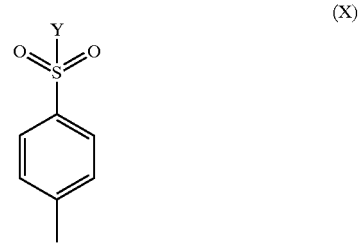

(X)

where Y is F, Cl or Br, preferably Cl, in a suitable solvent which is water-insoluble or sparingly water-soluble to give the acetylpyridine tosyl oxime of the formula (XI)

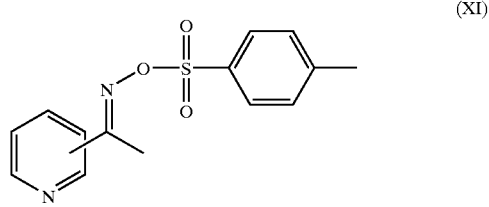

(XI)

the reaction proceeding in a biphasic mixture of water and suitable water-insoluble solvent, and the reaction optionally proceeding with the use of one or more phase transfer catalysts, for example quaternary ammonium or phosphonium salts, preferably a quaternary ammonium salt of the formula (XII) or a phosphonium salt of the formula (XIII) or a hydrate of a salt of the formula (II) or of the formula (XIII)

(XII)

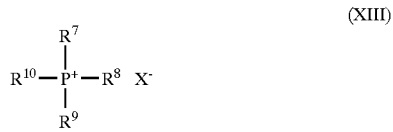

(XIII)

where $R^3$ to $R^{10}$ are the same or different and are each independently
a) $(C_1-C_{20})$-alkyl, straight-chain or branched,
b) benzyl or c) phenyl, and X⁻ is an anion, selected from the group consisting of fluoride, chloride, bromide, iodide, hydroxide, hydrogensulfate, tetrafluoroborate, acetate, trifluoromethanesulfonate, nitrate and hexafluoroantimonate.

The reaction in a biphasic mixture is preferably carried out with the use of one or more phase transfer catalysts, but also proceeds without phase transfer catalyst.

Process step (b) can be effected batchwise or continuously, preferably continuously, in which case the concentration of the compound of the formula (XI) which is critical from a safety point of view is kept low. The resulting mixture of solvent and aqueous phase is subsequently separated by the customary methods of phase separation. The aqueous phase contains the dissolved metal salts used. The aqueous phase is fed to a biological purification. Optionally, the aqueous phase can subsequently be washed once or more with a suitable water-insoluble solvent, and the solvent phases combined and further processed together. The solvent phase contains the compound of the formula (XI).

In process step (b), for 100 mol of 3-acetylpyridine oxime salt of the formula (IX), preference is given to using 0.1–50 mol, preferably 0.2–10 mol, of the phase transfer catalyst.

Examples of quaternary ammonium salts of the formula (XXII) are tetramethylammonium bromide, tetramethylammonium chloride, tetraethylammonium chloride, n-butyltriethylammonium chloride, methyltriisopropylammonium chloride, methyltri-n-butylammonium chloride (Aliquat® 175), methyltri-n-butylammonium bromide, methyltri-n-butylammonium hydrogensulfate, methyltetra-n-butylammonium chloride, methyltri-n-octylammonium chloride (Aliquat® 336), methyltri-n-octylammonium hydroxide, methyltricaprylammonium chloride, methyltricaprylammonium hydroxide, dimethylbenzyl ($C_8$–$C_{18}$)-alkyl chloride, tetra-n-propylammonium chloride, triethylhexylammonium chloride, triethyl-n-octylammonium chloride, triethyl-n-octylammonium bromide, triethyl-n-decylammonium bromide, triethyl-n-hexadecylammonium bromide, phenyltriethylammonium chloride, ethyltri-n-octylammonium bromide, tetra-n-butylammonium chloride, tetra-n-butylammonium bromide, tetra-n-butylammonium chloride, tetra-n-butylammonium hydrogensulfate, tetramethylammonium iodide, tetramethylammonium hydroxide pentahydrate, tetramethylammonium hydroxide, methyltriethylammonium bromide, tetramethylammonium chloride monohydrate, tetramethylammonium bromide, tetramethylammonium iodide, tetramethylammonium tetrafluoroborate, (n-hexyl)trimethylammonium bromide, phenyltrimethylammonium chloride, phenyltrimethylammonium iodide, benzyltrimethylammonium chloride, benzyltrimethylammonium iodide, benzyltrimethylammonium hydroxide, (n-octyl)trimethylammonium bromide, (N-nonyl)trimethylammonium bromide, tetra-n-propylammonium bromide, phenyltriethylammonium iodide, (n-decyl)trimethylammonium bromide, benzyltriethylammonium chloride, benzyltriethylammonium bromide, benzyltriethylammonium tetrafluoroborate, benzyltriethylammonium hydroxide, (n-dodecyl)trimethylammonium chloride, (n-dodecyl)trimethylammonium bromide, benzyltri-n-propylammonium chloride, tetra-n-butylammonium bromide, tetra-n-butylammonium iodide, tetra-n-butylammonium acetate, tetra-n-butylammonium hydrogensulfate, tetra-n-butylammonium hydroxide, tetra-n-butylammonium trifluoromethanesulfonate, (n-tetradecyl)trimethylammonium chloride, (n-tetradecyl)trimethylammonium bromide, (n-hexadecyl)trimethylammonium bromide, tetra-n-pentylammonium chloride, tetra-n-pentylammonium iodide, benzyltri-n-butylammonium chloride, benzyltri-n-butylammonium bromide, (n-hexadecyl)pyridinium chloride monohydrate, (n-hexadecyl)pyridinium bromide monohydrate, tetra-n-hexylammonium bromide, tetra-n-hexylammonium hydrogensulfate, tetra-n-octylammonium bromide, tetra-n-dodecylammonium iodide or tetra-n-dodecylammonium nitrate.

Examples of phosphonium salts of the formula (XIII) are tetra-n-butylphosphonium chloride, tetraphenylphosphonium bromide, methyltri-n-octylphosphonium chloride, methyltriphenylphosphonium bromide, ethyltri-n-octylphosphonium bromide, tetra-n-butylphosphonium bromide, tetraphenylphosphonium chloride, tetraphenylphosphonium iodide, tetraphenylphosphonium hexafluoroantimonate, tetraphenylphosphonium tetrafluoroborate, (n-hexadecyl)tri-n-butylphosphonium bromide or triphenylmethyltriphenylphosphonium chloride.

Suitable solvents which are water-immiscible or sparingly water-soluble or water-insoluble are, for example, aliphatic or aromatic hydrocarbons which are unsubstituted or substituted by one or more ($C_1$–$C_4$)-alkyl groups, for example methyl, or one or more substituents from the group of fluorine, chlorine and bromine, preferably toluene, xylene (as the pure isomers or mixtures of the isomers), ethylbenzene, heptane or dichloromethane. Also suitable are mixtures of the suitable solvents mentioned.

For 1 mol of p-toluenesulfonic acid derivative (X), preference is given to using from 0.6 to 1.1 kg of suitable solvent. In the reaction of 100 mol of acetylpyridine oxime salt of the formula (IX), preference is given to using 99–150 mol, more preferably 100–110 mol, of p-toluenesulfonic acid derivative (X).

The term biphasic mixture refers to the mixture of two liquid phases—aqueous phase which comprises the acetylpyridine oxime salt (IX) and the solvent phase which comprises the p-toluenesulfonic acid derivative (X). When a phase transfer catalyst is used, it may be present either in the aqueous phase or in the solvent phase, or be divided between the phases. The biphasic mixture is stirred and/or mixed by customary methods of batchwise or continuous process operation, so that good distribution of the phases is ensured.

The temperature for the reaction in process step (b) in a batchwise procedure is preferably 0–50° C., more preferably 5–30° C., and in a continuous procedure 0–60° C., more preferably 5–40° C.

In process step (c), the solvent phase comprising the acetylpyridine tosyl oxime of the formula (XI), after drying or without preceding drying, is metered into a mixture of alkali metal alkoxide, alkali metal hydroxide, alkaline earth metal alkoxide or alkaline earth metal hydroxide and an alcohol, where "alkoxide" means $R^1O^-$ and/or $R^2O^-$ and where alcohol means $R^1OH$ and/or $R^2OH$, and $R^1$ and $R^2$ are as defined in the compound of the formula (I), and converted to the 1-(pyridinyl)-1,1-dialkoxy-2-aminoethane derivative of the formula (I).

In process step (c), for 100 mol of the acetylpyridine tosyl, oxime of the formula (XI), preference is given to using 99–500 mol of an alkali metal alkoxide, more preferably 100–200 mol; or 99–500 mol of an alkali metal hydroxide, more preferably 100–300 mol; or 50–250 mol of an alkaline earth metal alkoxide, more preferably 50–100 mol, or 50–250 mol of an alkaline earth metal hydroxide, more preferably 50–150 mol.

In process step (c), preference is given to using alkali metal hydroxides or alkoxides, particularly lithium hydroxide, lithium methoxide, lithium ethoxide, sodium hydroxide, sodium methoxide, sodium ethoxide, potassium hydroxide, potassium methoxide, potassium ethoxide, cesium hydroxide, cesium methoxide or cesium ethoxide.

The choice of the alkoxide and/or of the alcohol depends on the introduction of the desired alkoxy groups. For example, for the preparation of 1-(pyridinyl)-1,1-dimethoxy-2-aminoethane, a mixture is used of an alkali metal or alkaline earth metal methoxide in methanol or an alkali metal hydroxide in methanol. For the preparation of the compound 1-(pyridinyl)-1-([1,3]dioxolane)-2-aminoethane in which $R^1$ and $R^2$ together with the oxygen atoms form a cyclic ketal, an alkali metal hydroxide in glycol, for example, is used.

For 1 mol of acetylpyridine oxime tosylate of the formula (XI), preference is given to using 0.3–3 kg, preferably 0.5–1.5 kg, of the corresponding alcohol. The conversion is effected, for example, within a temperature range of 0–90° C., more preferably at 10–60° C.

After the reaction, a portion of the solvent is initially distilled off, so that the p-toluenesulfonic acid salt by-product precipitates out at room temperature. The distillation is effected by customary methods. The solvent mixture which has been distilled off (distillate) can be reused directly for process step (c).

The p-toluenesulfonic acid alkali metal or alkaline earth metal salt is removed by customary filtration methods. The remaining solvent fractions are removed by distillation under atmospheric pressure or preferably under reduced pressure, by customary methods.

The amino ketal derivative of the formula (I) is subsequently optionally isolated in highly pure form either by vacuum distillation or rectification, or by crystallization from the distillation residue obtained in the preceding distillation. For example, a compound of the formula (I) in which $R_1$ and $R_2$ are each methyl can be purified by distillation.

The yield in the vacuum distillation or rectification can optionally be improved by adding a flux to the distillation residue. The term flux refers to a liquid or a waxy solid whose viscosity reduces on heating, thus improving the flow properties of the residue to be distilled, but at the same time has a considerably higher boiling point than the product to be distilled. The flux used is, for example, polyethylene glycols having a molecular weight greater than 400 (for example polyethylene glycol 600 or polyethylene glycol 1000), paraffins ($C_nH_{2n+2}$ where n>15), polyhydric alcohols (alcohols having more than one OH group, for example glycerol) or esters, for example bis-2-ethyl sebacate.

The crystallization can be effected by customary methods, with or without use of organic solvents. Melt or solvent processes may be used.

The advantages of the process according to the invention are, first, the direct isolation of the compounds of the formula (I) as a free base in high purity and very good yield; second, that the selected reaction conditions allow the oximation and the tosylation reaction to be carried out in a continuous procedure, which always generates only small amounts of the intermediate of the formula (XI) which is relevant from a safety point of view, without isolating the acetylpyridine tosyl oximes which are critical from a safety point of view as a solid, since, after a short delay time, they are converted directly in a continuous apparatus to the amino ketal of the formula (I) which is uncritical from a safety point of view; third, the preparation of the compounds of the formula (I) in high purity (greater than 97%) and yield (greater than 75% based on the acetylpyridine used) in the form of the free base in a manner which is suitable for the industrial scale; and fourth, the use of solvent which can be reused directly in the process in pure form or in the form of mixtures, so that the environmental implications are kept very small.

EXAMPLE 1

Preparation of 1-(3-pyridinyl)-1,1-dimethoxy-2-aminoethane, method 1

1(a) In a reactor, 174 g of 40% hydroxylammonium chloride solution, 121 g of 3-acetylpyridine and 245 g of 33% sodium hydroxide solution are reacted in a 3 component metering within a temperature range of 15–25° C. The resulting sodium salt solution of 3-acetylpyridine oxime is reacted with 2 g of methyltributylammonium chloride.

1(b) Subsequently, this solution is reacted in a continuous process (recycle method via static mixers with partial withdrawal) with a solution of 193 g of p-toluenesulfonyl chloride and 655 g of toluene, up to an internal temperature of 35–38° C. The resulting biphasic mixture is then passed through a separating zone and the solvent phase is separated from the aqueous phase.

1(c) The solvent phase is allowed to run directly into an initially charged solution of 940 g of methanol (or methanol/toluene mixture from the 1st solvent distillation, see below) and 216 g of 30% sodium methoxide solution. The temperature is kept within a range of 20–40° C. The reaction solution is allowed to continue to react for another 5–10 hours. The methanol was distilled out of the reaction mixture as an azeotropic mixture together with toluene (1 st solvent distillation) at 70–90° C. and atmospheric pressure. The azeotropic solvent mixture can be reused in the above-described reaction (see above). After the distillation, the distillation residue is cooled to 25° C. and the p-toluenesulfonic acid sodium salt is subsequently filtered off and washed with 85 g of toluene. The filtrate is subsequently concentrated by distillation under reduced pressure (approx. 100–200 mbar) up to an internal temperature of approx. 120–130° C. Subsequently, 10–20 g of polyethylene glycol 600 are added to the distillation residue and the 1-(3-pyridinyl)-1,1-dimethoxy-2-aminoethane is distilled off via a short column as a water-clear liquid at 1–10 mbar at an internal evaporator temperature of 100–160° C. 157.3 g of 1-(3-pyridinyl)-1,1-dimethoxy-2-aminoethane are obtained having a purity of 98–99% (determined in comparison to a reference standard by means of titration, HPLC-MS and NMR). This corresponds to a yield of 85% of theory, based on the 3-acetylpyridine used.

EXAMPLE 2

Preparation of 1-(3-pyridinyl)-1,1-dimethoxy-2-aminoethane, method 2

2(a) In a reactor, 174 g of 40% hydroxylammonium chloride solution, 121 g of 3-acetylpyridine and 245 g of 33% sodium hydroxide solution are reacted in a 3-component metering within a temperature range of 15–25° C. The resulting sodium salt solution of 3-acetylpyridine oxime is added with 2 g of methyltributylammonium chloride.

2(b) Subsequently, this solution is reacted in a continuous process (recycle method via static mixers with partial withdrawal) with a solution of 193 g of p-toluenesulfonyl chloride and 655 g of toluene, up to an internal temperature of 35–38° C. The resulting biphasic mixture is then passed through a separating zone and the solvent phase is separated from the aqueous phase.

2(c) The solvent phase is allowed to run directly into an initially charged solution of 940 g of methanol (or methanol/toluene mixture from the 1st solvent distillation, see below) and 48 g of sodium hydroxide. The temperature is kept within a range of 20–40° C. The reaction solution is allowed to continue to react for another 5–10 hours. The methanol was distilled out of the reaction mixture as an azeotropic mixture together with toluene (1st solvent distillation). The azeotropic solvent mixture can be reused in the above-described reaction (see above). After the distillation, the distillation residue is cooled to 25° C. and the p-toluenesulfonic acid sodium salt is subsequently filtered off and washed with 85 g of toluene. The filtrate is subsequently concentrated by distillation under reduced pressure (approx. 100–200 mbar) up to an internal temperature of approx. 120–130° C. Subsequently, 10–20 g of polyethylene glycol 600 are added to the distillation residue and the 1-(3-pyridinyl)-1,1-dimethoxy-2-amino-ethane is distilled off via a short column as a water-clear liquid at 1–10 mbar at an internal evaporator temperature of 100–160° C. 148 g of 1-(3-pyridinyl)-1,1-dimethoxy-2-aminoethane are obtained having a purity of 98–99% (determined in comparison to a reference standard by means of titration, HPLC-MS and NMR). This corresponds to a yield of 80% of theory, based on the 3-acetylpyridine used.

What is claimed is:

1. A process for preparing 1-(pyridinyl)-1,1-dialkoxy-1-aminoethane derivatives of the formula (I)

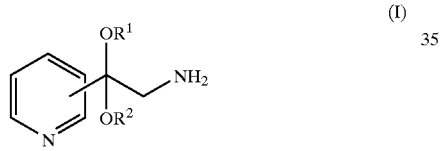

wherein $R^1$ and $R^2$ are each independently straight-chain or branched ($C_1$–$C_6$)-alkyl, or $R^1$ and $R^2$ together with the oxygen atoms form a cyclic ketal wherein $R^1$ and $R^2$ together are a ($C_2$–$C_4$)-alkylidene group, and wherein the pyridine radical is substituted in the 2-, 3- or 4-position, comprising:

(a), converting acetylpyridine of the formula (V) using an aqueous solution of a hydroxylammonium compound or an aqueous solution of hydroxylamine, in the presence of an inorganic base, to the acetylpyridine oxime metal salt of the formula (IX) wherein n is 1 or 2 and $M^{n+}$ is an alkali metal or alkaline earth metal ion

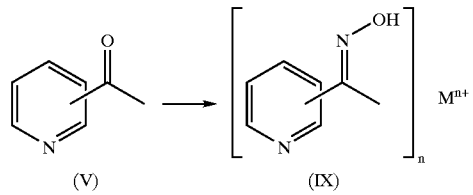

(b), reacting the acetylpyridine metal salt of the formula (IX) with a solution of a p-toluenesulfonic acid derivative (X) containing a leaving group Y

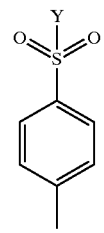

wherein Y is F, Cl or Br, in a suitable solvent which is water-immiscible or sparingly water-soluble or water-insoluble to give the acetylpyridine tosyl oxime of the formula (XI)

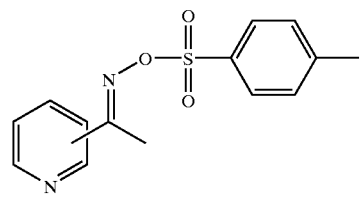

the reaction proceeding in a biphasic mixture of water and suitable solvent, optionally with the use of one or more phase transfer catalysts, (c), reacting acetylpyridine tosyl oxime of the formula (XI) with a mixture of an alkali metal alkoxide, an alkali metal hydroxide, an alkaline earth metal alkoxide or an alkaline earth metal hydroxide with an alcohol to produce a compound of the formula (I), wherein alkoxide is $R^1O^-$ or $R^2O^-$, and wherein alcohol is $R^1OH$ or $R^2OH$, and $R^1$ and $R^2$ are each as defined for the compound of the formula (I); and conducting the process continuously or batchwise independently for each process step (a) to (c).

2. The process as claimed in claim 1, wherein the pyridine radical is substituted in the 3-position.

3. The process as claimed in claim 1, wherein $R^1$ and $R^2$ are each ($C_1$–$C_6$)-alkyl.

4. The process as claimed in claim 1, wherein, the hydroxylammonium compound in process step (a) is selected from the group consisting of hydroxylamine, hydroxylammonium chloride and hydroxylammonium sulfate.

5. The process as claimed in claim 1, wherein, in process step (a), $M^{n+}$ is $Li^+$, $Na^+$, $K^+$ or $Ca^{2+}$.

6. The process as claimed in claim 1, wherein, in process step (a), the inorganic base is selected from the group consisting of lithium hydroxide, sodium hydroxide, sodium carbonate, sodium hydrogencarbonate, potassium hydroxide, potassium carbonate and calcium hydroxide.

7. The process as claimed in claim 1, wherein, in process step (b), the leaving group Y is Cl.

8. The process as claimed in claim 1, wherein, in process step (b), the phase transfer catalyst is a quaternary ammonium salt of the formula (XII) or a phosphonium salt of the formula (XIII)

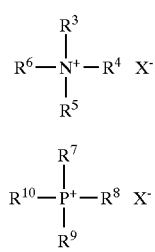

(XII)

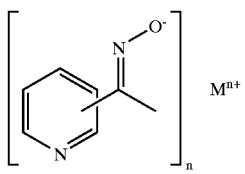

(XIII)

where $R^3$ to $R^{10}$ are the same or different and are each independently
a) $(C_1-C_{20})$-alkyl, straight-chain or branched,
b) benzyl or
c) phenyl, and $X^-$ is an anion, selected from the group consisting of fluoride, chloride, bromide, iodide, hydroxide, hydrogensulfate, tetrafluoroborate, acetate, trifluoromethanesulfonate, nitrate and hexafluoroantimonate.

9. The process as claimed in claim 1, wherein, in process step (c), the alkali or alkaline earth metal alkoxide, and alkali or alkaline earth metal hydroxide are selected from the group consisting of lithium hydroxide, lithium methoxide, lithium ethoxide, sodium hydroxide, sodium methoxide, sodium ethoxide, potassium hydroxide, potassium methoxide, potassium ethoxide, cesium hydroxide, cesium methoxide and cesium ethoxide.

10. The process as claimed in claim 1, wherein, in process step (c), the acetylpyridine tosyl oxime of the formula (XI) is used without prior drying.

11. A process for preparing an acetylpyridine oxime metal salt of the formula (IX)

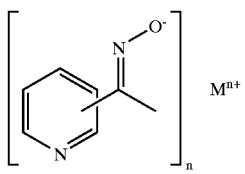

(IX)

wherein n is 1 or 2 and $M^{n+}$ is an alkali metal ion or alkaline earth metal ion, and where the pyridine radical is substituted in the 2-, 3- or 4-position,
comprising:
converting acetylpyridine of the formula (V)

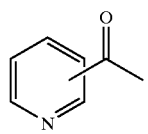

(V)

using an aqueous solution of hydroxylamine or of a hydroxylammonium compound, with the addition of an inorganic base, to the acetylpyridine oxime metal salt of the formula (IX); and
conducting the process continuously or batchwise.

12. The process as claimed in claim 11, wherein the pyridine radical is substituted in the 3-position.

13. The process as claimed in claim 11, wherein $M^{N+}$ is $Li^+$, $Na^+$, $K^+$ or $Ca^{2+}$.

14. The process as claimed claim 11, wherein the inorganic base is lithium hydroxide, sodium hydroxide, sodium carbonate, sodium hydrogencarbonate, potassium hydroxide, potassium carbonate or calcium hydroxide.

15. The process as claimed in claim 11, which is conducted continuously.

16. A process for preparing the compound of the formula (XI)

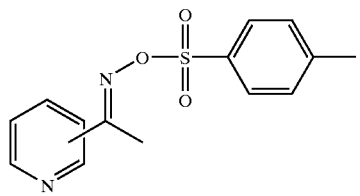

(XI)

wherein the pyridine radical is substituted in the 2-, 3- or 4-position,
comprising:
reacting the acetylpyridine metal salt of the formula (IX)

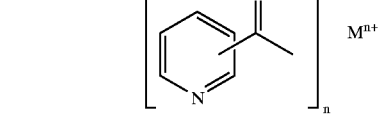

(IX)

wherein n is 1 or 2 and $M^{n+}$ is an alkali metal ion or alkaline earth metal ion with a solution of a p-toluenesulfonic acid derivative (X) containing a leaving group Y

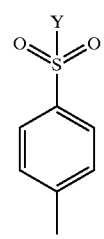

(X)

wherein Y is F, Cl or Br, in a suitable solvent which is water-insoluble or sparingly water-soluble to give the acetylpyridine tosyl oxime of the formula (XI),
the reaction proceeding in a biphasic mixture of water and suitable water-insoluble solvent, and the reaction proceeding optionally with the use of one or more phase transfer catalysts; and conducting the process continuously or batchwise.

17. The process as claimed in claim 16, which proceeds with the use of one or more phase transfer catalysts, and wherein the phase transfer catalyst is a quaternary ammonium salt of the formula (XII) or a phosphonium salt of the formula (XIII)

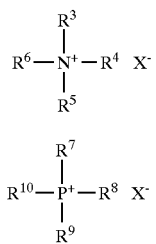

wherein $R^3$ to $R^{10}$ are the same or different and are each independently a) $(C_1-C_{20})$-alkyl, straight-chain or branched,
b) benzyl or
c) phenyl, and $X^-$ is an anion, selected from the group consisting of fluoride, chloride, bromide, iodide, hydroxide, hydrogensulfate, tetrafluoroborate, acetate, trifluoromethanesulfonate, nitrate and hexafluoroantimonate, preferably methyltributylammonium chloride.

18. The process as claimed in claim 16, wherein the pyridine radical is substituted in the 3-position.

* * * * *